United States Patent
Tomita et al.

(10) Patent No.: US 6,187,958 B1
(45) Date of Patent: Feb. 13, 2001

(54) AMINO GROUP-CONTAINING THIOLS AND METHOD FOR PRODUCTION THEREOF

(75) Inventors: Takashi Tomita, Takatsuki; Tsunemasa Ueno, Ikeda, both of (JP); Daniel Bernard, Courbevoie (FR)

(73) Assignee: Nippon Shokubai Co., LTD (JP)

( * ) Notice: Under 35 U.S.C. 154(b), the term of this patent shall be extended for 0 days.

(21) Appl. No.: 09/058,729

(22) Filed: Apr. 10, 1998

(30) Foreign Application Priority Data

Apr. 11, 1997 (FR) .................................................. 97 04492

(51) Int. Cl.$^7$ ................................................ C07C 321/00
(52) U.S. Cl. ............................................ 564/500; 564/501
(58) Field of Search ..................... 564/501, 500

(56) References Cited

U.S. PATENT DOCUMENTS

| | | |
|---|---|---|
| 3,387,953 | 6/1968 | Bouffard . |
| 3,919,290 | * 11/1975 | Egger et al. .......................... 260/481 |
| 4,808,755 | * 2/1989 | Wirth et al. ........................... 564/501 |

FOREIGN PATENT DOCUMENTS 631 016    6/1936    (DE) .

OTHER PUBLICATIONS

H.R. Snyder et al., "The synthesis of amino mercaptans from oleum sulphides" Journal of the American Chemical Society, vol. 69, No. 11, Nov. 1947, pp. 2672–2674.

R.J. Wineman et al., "Thiomethylation of amines with ethylene sulphide", Journal of Organic Chemistry, vol. 27, No. 12, Dec. 1962, pp. 4222–4226.

R.T. Wragg, "Metal thiolates as initiators for the polymerisation of aklylene sulphides" Journal of the Chemical Society, Section–C: Organic Chemistry, 1969, pp. 2087–2092.

M.A. Allakhverdiev et al., "Synthesis and properties of alkoxy–substituted 1–aminopropane–2–thiols", Russian Journal of Applied Chemistry, vol. 67, No. 11, part 2, Nov. 1994, pp. 1641–1644.

\* cited by examiner

*Primary Examiner*—Samuel Barts
(74) *Attorney, Agent, or Firm*—Fish & Richardson P.C.

(57) ABSTRACT

These amino group-containing mono- or dithiols are represented by formula (I). In order to prepare them, ethylene sulfide is reacted with at least one compound of formula (II), the average number of moles of ethylene sulfide added corresponding to the total m+n, and possibly the compound of formula (I) as obtained is further reacted with ethylene sulfide in order to increase the value of m+n.

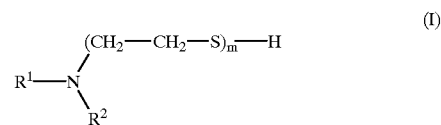

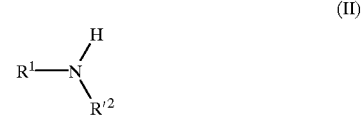

$R^1$ stands for a straight or branched alkyl or alkenyl group having 10 to 30 carbon atoms; $R^2$ stands for a straight or branched alkyl or alkenyl group having 10 to 30 carbon atoms, or a $—(CH_2—CH_2—S)_n—H$ group; m and n, which are identical or different, each represent 0 or an integer in the range of 1 to 10 and satisfy $1.6 \leq m+n \leq 20$; $R'^2$ stands for a hydrogen atom in which case $R^2$ in formula (I) will represent $—(CH_2—CH_2—S)_n—H$, or a straight or branched alkyl or alkenyl group having 10 to 30 carbon atoms, in which case it will remain unchanged in the compound of the formula (I).

18 Claims, 6 Drawing Sheets

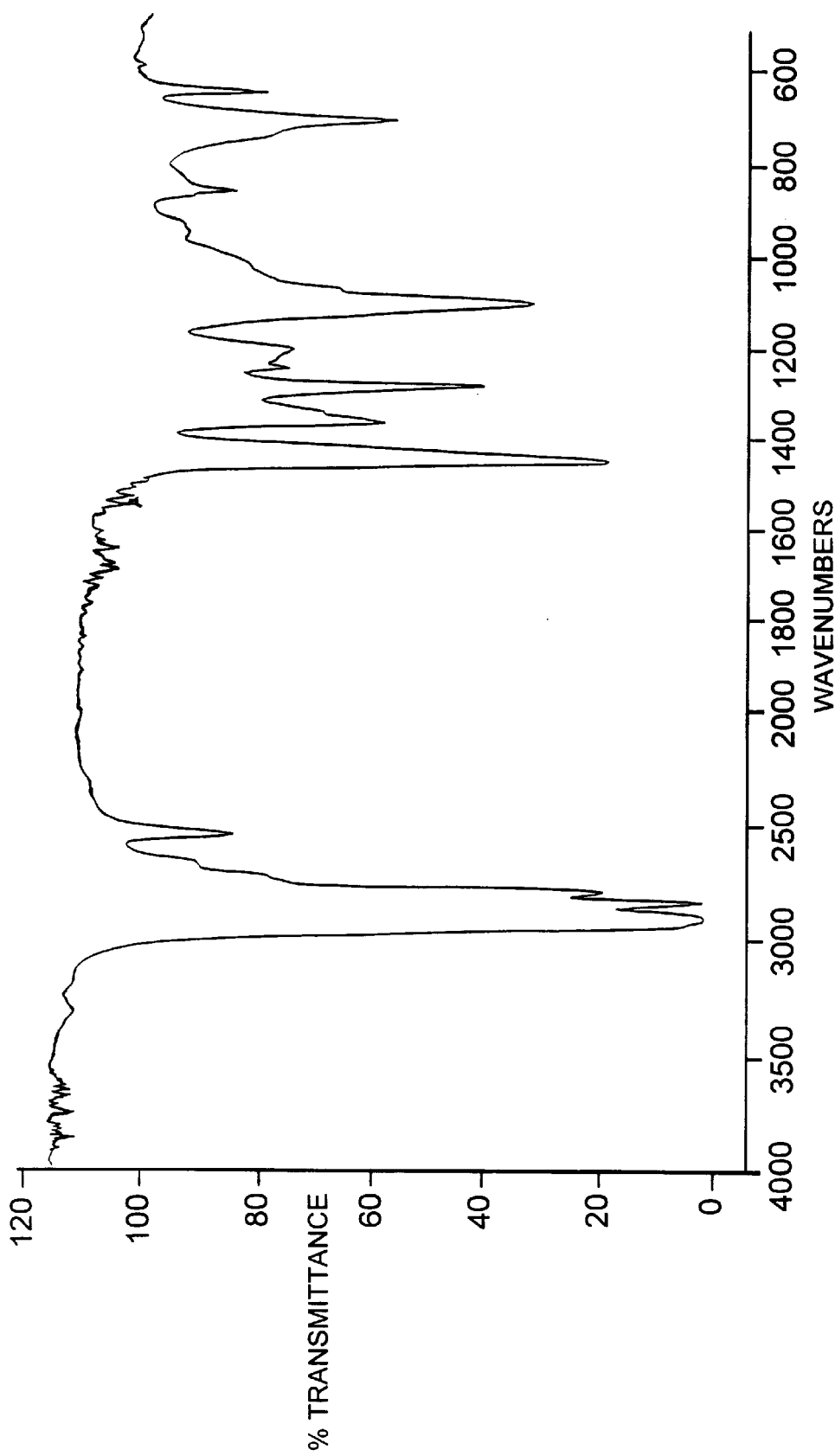
FIG. 1 INFRARED ABSORPTION SPECTRUM (NaCl) OF PRODUCT OF EXAMPLE 1

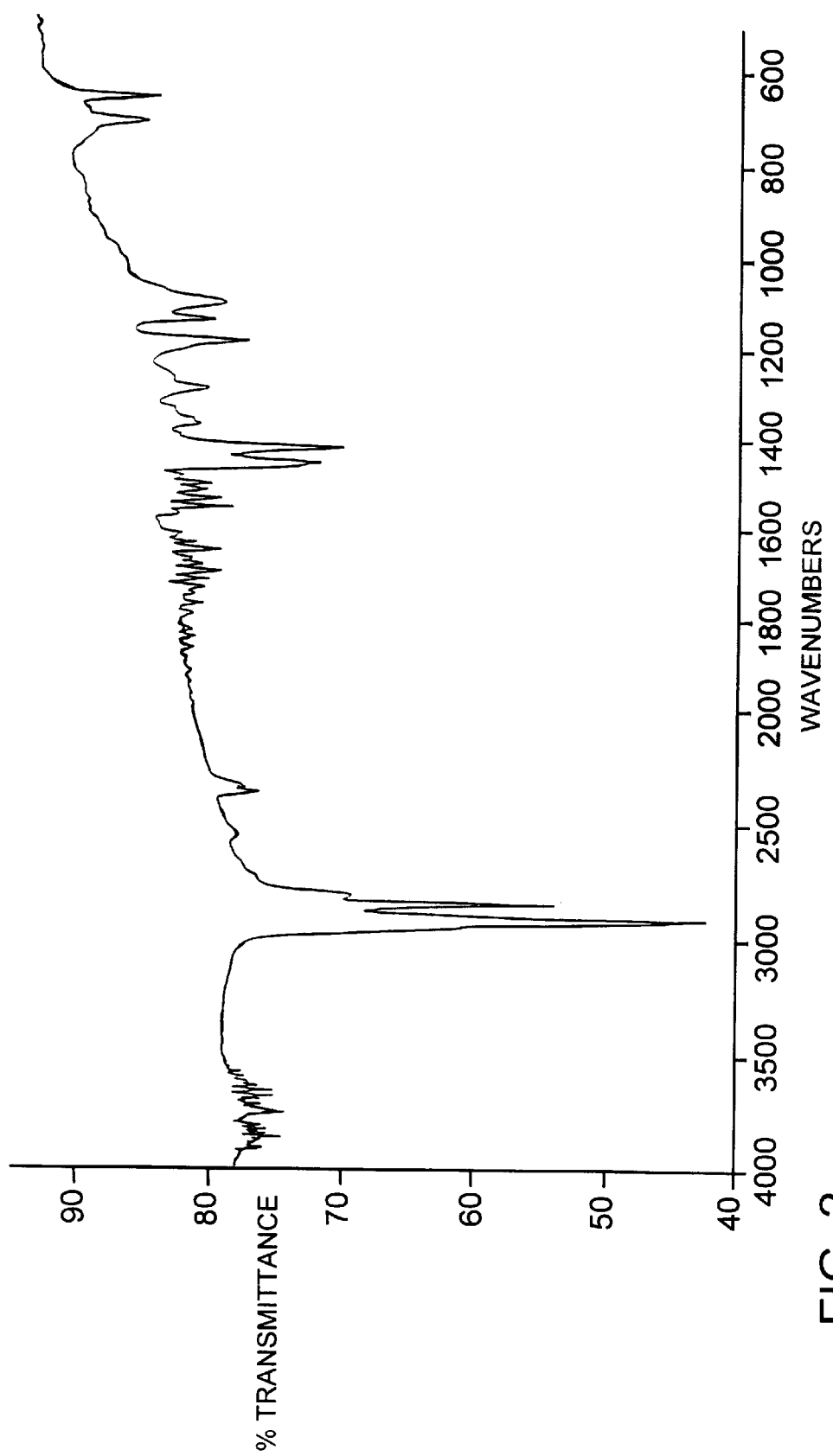
FIG. 2 INFRARED ABSORPTION SPECTRUM (NaCl) OF PRODUCT OF EXAMPLE 2

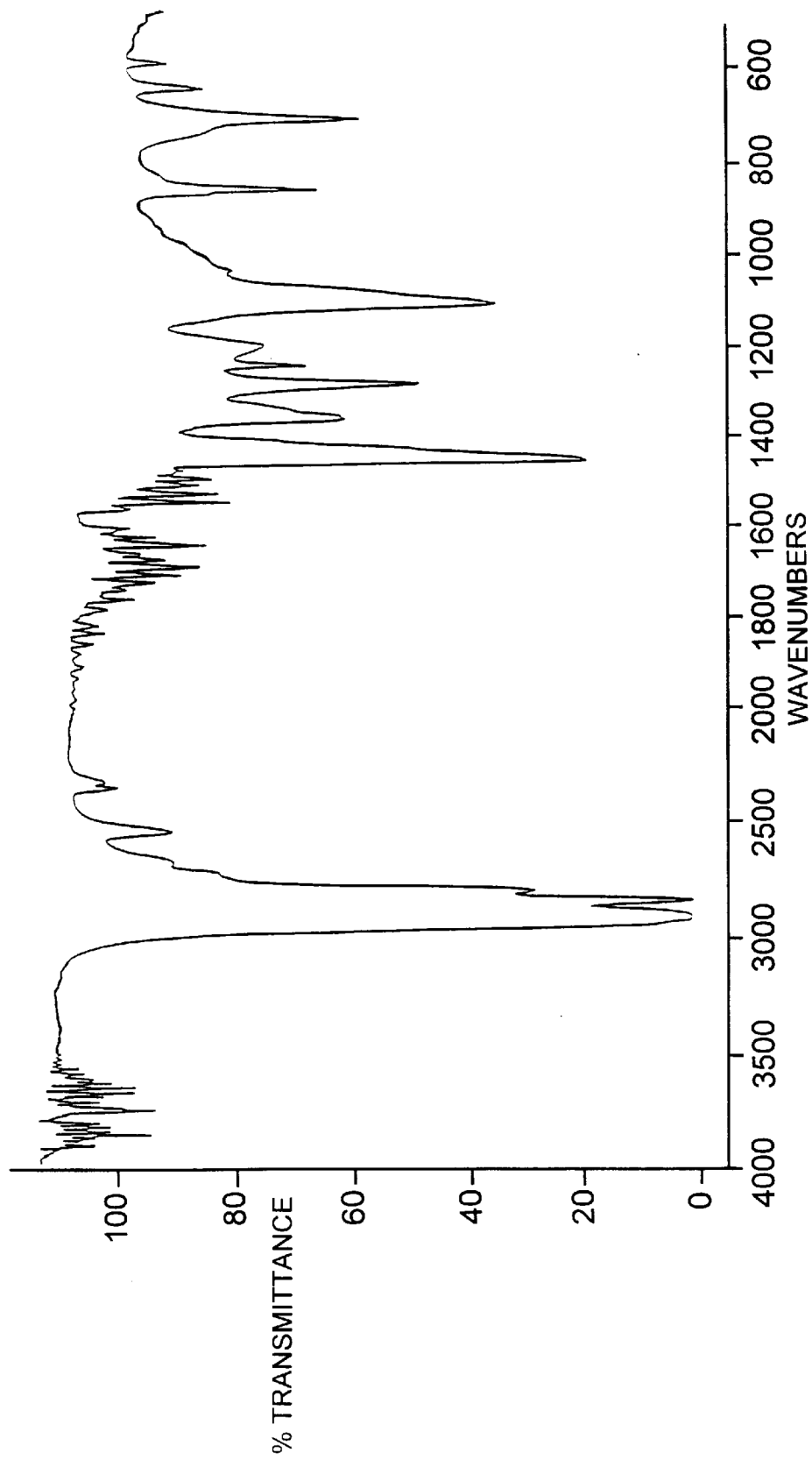
FIG. 3  INFRARED ABSORPTION SPECTRUM (NaCl) OF PRODUCT OF EXAMPLE 3

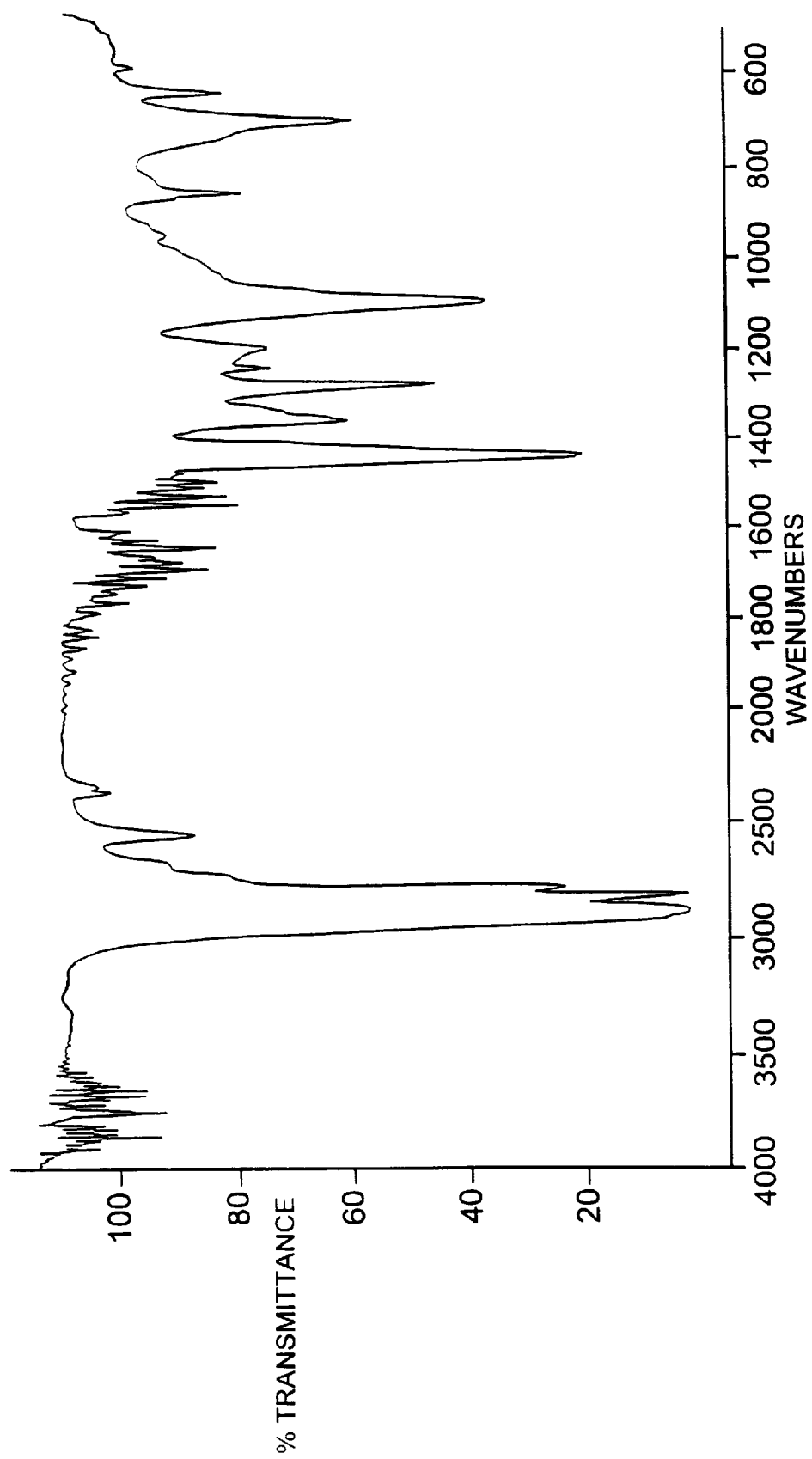
FIG. 4    INFRARED ABSORPTION SPECTRUM (NaCl) OF PRODUCT OF EXAMPLE 4

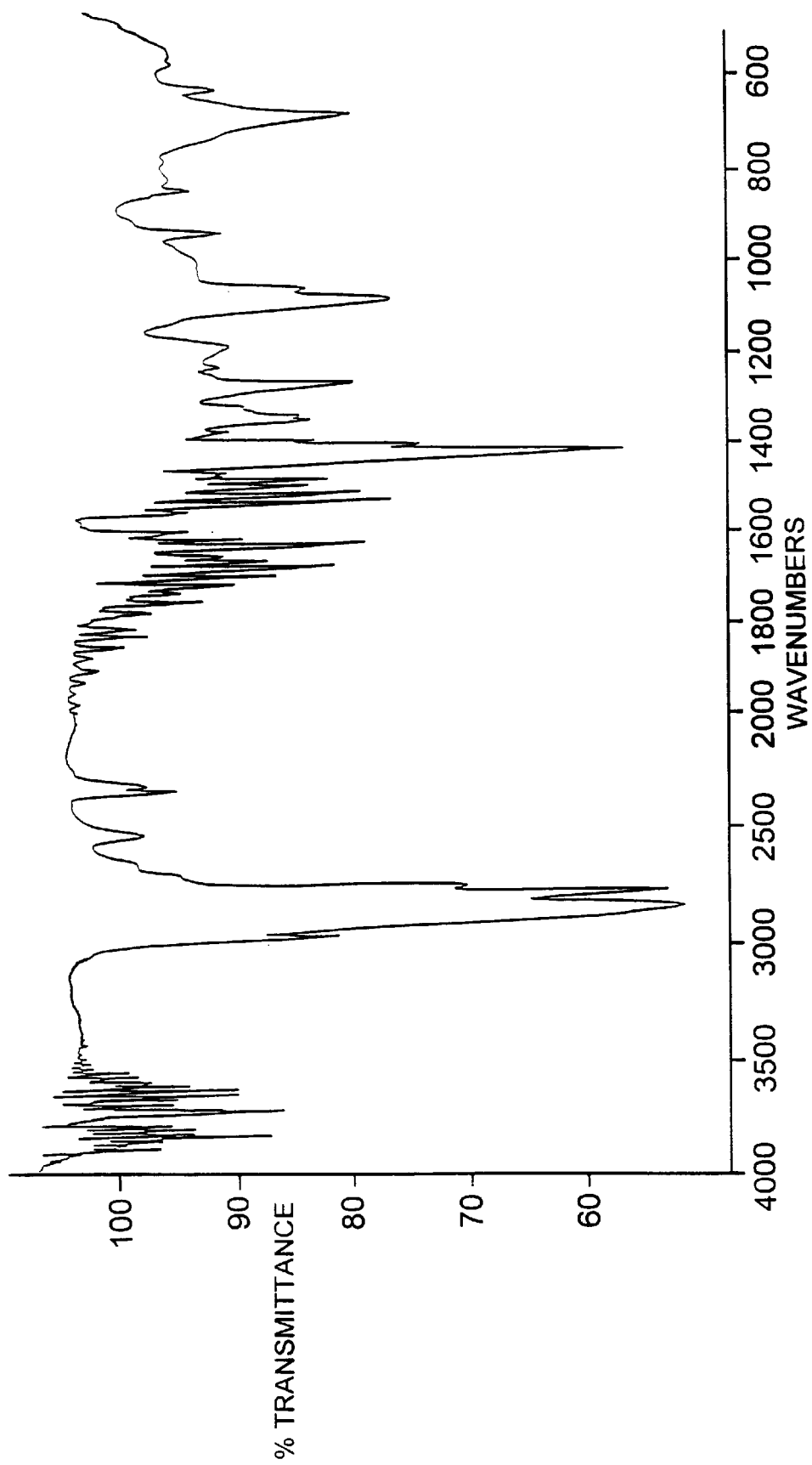
FIG. 5 INFRARED ABSORPTION SPECTRUM (NaCl) OF PRODUCT OF EXAMPLE 5

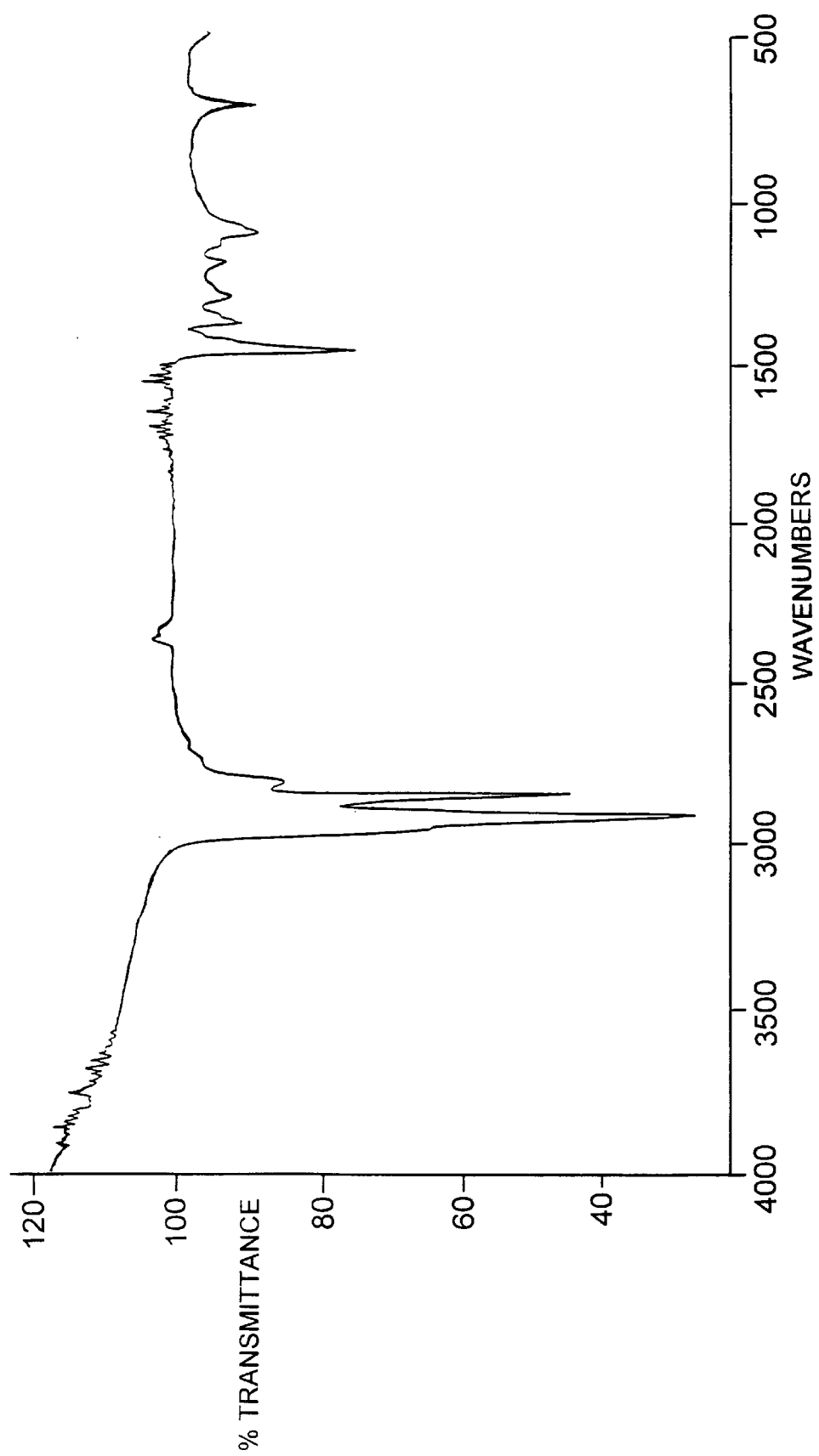
FIG. 6  INFRARED ABSORPTION SPECTRUM (NaCl) OF PRODUCT OF EXAMPLE 6

AMINO GROUP-CONTAINING THIOLS AND METHOD FOR PRODUCTION THEREOF

FIELD OF THE INVENTION

The present invention relates to novel amino group-containing thiols and also to a method for the production thereof. These novel thiols are compounds which contain a long-chain alkyl or alkenyl group in the molecule thereof and which show a high reactivity.

BACKGROUND OF THE INVENTION

Various thiol type compounds have been disclosed to date. Particularly, thiol compounds containing an amino group have long attracted interest and found utility in a wide range of applications because of their unique qualities. For example, cysteamine, a compound that has the simplest structure of all such amino group-containing thiol compounds, is useful as an intermediate for medicines and as an agent for treating hair and imparting permanent wave thereto. N-alkyl substituted compounds, namely amino group-containing thiols, which incorporate therein an alkyl group, have been found useful in the field of printing (as disclosed in JP-A-06-127,168), as intermediates for medicines (as disclosed in JP-A-48-44,244), in the field of photography (as disclosed in U.S. Pat. No. 3,221,013), and in the field of rubber (as reported in J. Am. Chem. Soc., Vol. 69, page 2672, 1947), for example.

Novel thiols containing an amino group, therefore, have reasons to promise a great usefulness. N-Methyldodecylaminoethane thiol, which is disclosed in DE 631,016 and undecylaminoethane thiol, which is reported in J. Org. Chem., Vol. 27, page 4222, 1962, are, for the time being, the only concrete examples of amino group-containing thiols that incorporate therein a long-chain alkyl or alkenyl group.

SUMMARY OF THE INVENTION

An object of the present invention, therefore, is to provide novel amino group-containing thiol compounds, which incorporate therein a long-chain alkyl or alkenyl group, and which are expected to find utility in various applications, said thiols having furthermore proved themselves useful as intermediates for synthesis.

BRIEF DESCRIPTION OF THE DRAWINGS

FIG. 1 is an infrared absorption spectrum of the product of Example 1.

FIG. 2 is an infrared absorption spectrum of the product of Example 2.

FIG. 3 is an infrared absorption spectrum of the product of Example 3.

FIG. 4 is an infrared absorption spectrum of the product of Example 4.

FIG. 5 is an infrared absorption spectrum of the product of Example 5.

FIG. 6 is an infrared absorption spectrum of the product of Example 6.

DETAILED DESCRIPTION

The object mentioned above is accomplished by an amino group-containing mono- or dithiol, characterized by the fact it is represented by formula (I):

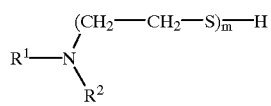

wherein:
$R^1$ stands for a straight or branched alkyl or alkenyl group having 10 to 30 carbon atoms; and
$R^2$ stands for a straight or branched alkyl or alkenyl group having 10 to 30 carbon atoms, or a —$(CH_2-CH_2-S)_n$—H group
m and n, which are identical or different, each represent 0 or an integer in the range of 1 to 10 and satisfy $1.6 \leq m+n \leq 20$;
and by the mixtures of such mono- and/or dithiols.

Preferably, the total number m+n is not in excess of 10.

$R^1$ can especially stand for the residue of a primary complex fatty amine, such as a copra chain or an oleic chain, $R^2$ standing then for a —$(CH_2-CH_2-S)_n$—H group, the resulting dithiol being then under the form of a mixture; $R^1$ and $R^2$ can also simultaneously stand for residues of a secondary complex fatty amine, the resulting monothiol then being in the form of a mixture.

The amino group-containing thiols of the present invention have a thioethylene unit without alkyl substituents. The unit has moderate hydrophilicity and the thiols are relatively easy to formulate such as by making a water dispersion. In addition, the thiols have significant surface active properties, corrosion inhibition performance and dispersibility derived from their structure. Therefore, the thiols of the present invention are suitable in such fields as the oil industry, and for use as corrosion and scale inhibitors, detergents, and for water and metal treatment.

Another object of the present invention is a method for the production of a mono- or dithiol as defined above, characterized by the fact that ethylene sulfide is reacted with at least one compound of formula (II)

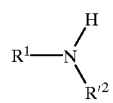

wherein:
$R^1$ has the above-mentioned meaning; and
$R'^2$ stands for a hydrogen atom in which case $R^2$ in the compound of formula (I) will represent —$(CH_2-CH_2-S)_n$—H, or a straight or branched alkyl or alkenyl group having 10 to 30 carbon atoms, in which case it will remain unchanged in the compound of formula (I),
the average number of moles of ethylene sulfide added corresponding to the total m+n,
and possibly the compound of formula (I) as obtained is further reacted with ethylene sulfide in order to increase the value of m+n.

Ethylene sulfide is generally used in an amount which corresponds to a ratio within a range of 1.6 to 20 (preferably 1.6 to 10) equivalents per equivalent of hydrogen on the primary or secondary amino group in the amine (II) as raw material.

The present invention relates also generally to the adducts of ethylene sulfide to at least one compound of formula (II).

The number of moles of ethylene sulfide which are added to one mole of compound (II) is at most equal to the number of moles of ethylene sulfide which are fed per mole of compound (II) as fed.

The compound(s) of formula (II) can be advantageously selected from among decyl amine, undecyl amine, lauryl amine, myristyl amine, cetyl amine, stearyl amine, primary amines derived from a fatty acid obtained from a coconut oil (copra oil), primary amines derived from oleic acid, primary amines derived from a fatty acid obtained from a soybean oil, didecyl amine, diundecyl amine, dilauryl amine, dimyristyl amine, dicetyl amine, distearyl amine, secondary amines derived from a fatty acid obtained from a coconut oil (copra oil), secondary amines derived from oleic acid and secondary amines derived from a fatty acid obtained from a soybean oil.

This reaction is generally carried out in an organic solvent which is inert under the conditions of the reaction; however, the use of this solvent may be omitted. Organic solvents that can be used in the present invention include: aromatic compounds such as benzene, toluene and xylene, ether type compounds such as diethyl ether, ethyl isobutyl ether, tetrahydrofuran and dioxane, alcohol type compounds such as methanol, ethanol, n-propanol, isopropanol, n-butanol, t-butanol, heptanol, 2-ethylhexanol and cyclohexanol, nitrile type compounds such as acetonitrile and benzonitrile, amide type compounds such as N,N-dimethylformamide and N-methylpyrrolidone, and dimethyl sulfoxide.

To obtain a compound having not more than 2 moles of ethylene sulfide added to one mole of an amine compound of formula (II) with a high yield while avoiding the formation of a product resulting from the addition of opened ethylene sulfide cycles to themselves, it is appropriate to use an ether type solvent such as dioxane or tetrahydrofuran. For the efficient manufacture of a product having not less than two moles of ethylene sulfide added thereto, since the reaction performed in an ether type solvent alone proceeds at a very low rate, it is appropriate to carry out the reaction in a polar solvent such as N,N-dimethyl formamide, acetonitrile, benzonitrile and dimethyl sulfoxide or in a mixed solvent consisting of the polar solvent and the ether type solvent.

The reaction temperature is generally in the range of 10 to 200° C., preferably in the range of 50 to 120° C. If the reaction temperature is less than 10° C., the reaction rate will be unduly low. Conversely, if the reaction temperature exceeds 200° C., the product resulting from the adding of opened ethylene sulfide cycles to themselves and some by-products will be generated in an amount so large as to bring about a conspicuously lowered yield.

EXAMPLES

The following Examples illustrate the present invention without however restricting the scope thereof. In these examples, ethylene sulfide will be simply referred to as ES. The average value of m+n, which is the average number of moles of ES added to one mole of amine, was calculated on the basis of NMR analysis.

Example 1

Preparation of a Compound of Formula:

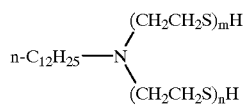

the average value of m+n being 2.

In a three-neck flask provided with a stirring device, a thermometer, a reflux condenser, and a dropping funnel, 30.0 g (162 mmols) of lauryl amine and 49.5 g of dioxane were placed, heated to 107° C. and refluxed. To the resultant reaction mixture kept at this temperature, 19.5 g (324 mmols) of ES was added dropwise over a period of four hours. After the dropwise addition was completed, the combined compounds were left reacting at the same temperature for four hours. After the reaction was completed, the resultant reaction solution was distilled to expel the solvent by evaporation, to obtain 48.2 g of a colorless transparent liquid (yield 97%).

The results obtained by the NMR analysis and the average number of moles of ES added for the product consequently obtained are shown in Table 1. The infrared absorption spectrum of this product is shown in FIG. 1.

TABLE 1

| | |
|---|---|
| $^1$H NMR CDCl$_3$ δ (ppm) | 0.88 (3.0 H), 1.18–1.80 (22.0 H), 2.38–2.83 (10.0 H) |
| Average number of moles of ES added | 2.0 |

Example 2

Preparation of a Compound of Formula:

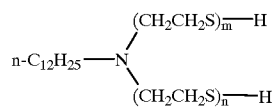

the average value of m+n being 5.

In a three-neck flask provided with a stirring device, a thermometer, a reflux condenser, and a dropping funnel, 30.0 g (92 mmols) of the ES adduct of lauryl amine (average number of added ES of 2.3) obtained by substantially the same procedure as in Example 1, 25.0 g of acetonitrile, and 5.0 g of dioxane were placed and heated to 78° C. To the resultant reaction mixture kept at this temperature, 16.6 g (276 mmols) of ES was added dropwise over a period of 40 minutes. After the dropwise addition was completed, the combined compounds were left reacting at the same temperature for 3.5 hours. After this reaction was completed, the resultant reaction solution was returned to normal room temperature and filtered to expel 4.8 g of white solids insoluble in the solvent. The filtrate was distilled to expel the solvent, to obtain 40.5 g of a light yellow waxy product (yield 87%).

The results obtained by the NMR analysis and the average number of moles of ES added for the product consequently obtained are shown in Table 2. The infrared absorption spectrum of this product is shown in FIG. 2.

TABLE 2

| $^1$H NMR CDCl$_3$ δ (ppm) | 0.88 (3.0 H), 1.20–1.80 (22.0 H), 2.40–2.89 (22.0 H) |
|---|---|
| Average number of moles of ES added | 5.0 |

Example 3
Preparation of a Compound of Formula:

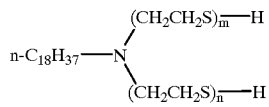

the average value of m+n being 2.3.

A white waxy product was obtained in the amount of 44.0 g (yield 78%) by following the procedure of Example 1 while using 30.8 g (111 mmols) of stearyl amine and 25.4 g (423 mmols) of ES as reactants and 44.7 g of dioxane as a solvent.

The results obtained by the NMR analysis and the average number of moles of ES added for the product consequently obtained are shown in Table 3. The infrared absorption spectrum of this product is shown in FIG. 3.

TABLE 3

| $^1$H NMR CDCl$_3$ δ (ppm) | 0.88 (3.0 H), 1.20–1.76 (34.0 H), 2.38–2.78 (11.4 H) |
|---|---|
| Average number of moles of ES added | 2.3 |

Example 4
Preparation of a Compound of Formula:

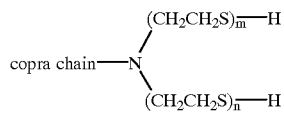

the average value of m+n being 2.0.

A slightly whitely turbid liquid was obtained in the amount of 38.9 g (yield 73%) by following the procedure of Example 1 while using 25.0 g (124 mmols) of an aliphatic primary amine originating in a coconut oil (total amine content of 4.98 meq/g determined by non-aqueous titration) and 28.4 g (472 mmols) of ES as reactants and 53.4 g of dioxane as a solvent.

The results obtained by the NMR analysis and the average number of moles of ES added for the product consequently obtained are shown in Table 4. The infrared absorption spectrum of this product is shown in FIG. 4.

TABLE 4

| $^1$H NMR CDCl$_3$ δ (ppm) | 0.88 (3.0 H), 1.20–1.80 (23.2 H), 2.38–2.86 (10.0 H) |
|---|---|
| Average number of moles of ES added | 2.0 |

Example 5
Preparation of a Compound of Formula:

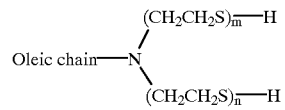

the average value of m+n being of 1.9.

A reddish brown liquid was obtained in the amount of 36.3 g (yield 94%) by following the procedure of Example 1 while using 25.0 g (92 mmols) of an aliphatic primary amine originating in oleic acid (total amine content 3.69 meq/g determined by non-aqueous titration) and 13.8 g (230 mmols) of ES as reactants and 38.8 g of dioxane as a solvent.

The results obtained by the NMR analysis and the average number of moles of ES added for the product consequently obtained are shown in Table 5. The infrared absorption spectrum of this product is shown in FIG. 5.

TABLE 5

| $^1$H NMR CDCl$_3$ δ (ppm) | 0.90 (3.0 H), 1.20–2.10 (28.2 H), 2.38–2.85 (9.6 H), 5.30–5.42 (2.0 H) |
|---|---|
| Average number of moles of ES added | 1.9 |

Example 6
Preparation of Compound of Formula:

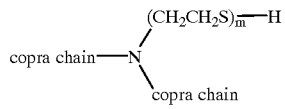

the average value of m being 1.7.

A white turbid liquid was obtained in the amount of 31.8 g (yield 84%) by following the procedure of Example 1 while using 30.0 g (65 mmols) of an ES adduct (average number of moles of ES added 0.75) of an aliphatic secondary amine originating in a coconut oil obtained substantially in the same manner as in Example 1 and 7.8 g (130 mmols) of ES as reactants and 18.9 g of dioxane and 18.9 g of N,N-dimethyl formamide as solvents.

The results obtained by the NMR analysis and the average number of added ES of the product consequently obtained are shown in Table 6. The infrared absorption spectrum of this product is shown in FIG. 6.

TABLE 6

| $^1$H NMR CDCl$_3$ δ (ppm) | 0.88 (6.0 H), 1.20–1.78 (47.3 H), 2.36–2.83 (10.8 H) |
|---|---|
| Average number of moles of ES added | 1.7 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A dithiol compound comprising an amino group and having the formula (I):

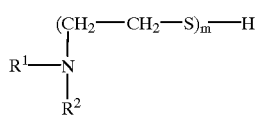

wherein
   $R^1$ is a straight or branched alkyl or alkenyl group having 10 to 30 carbon atoms; and
   $R^2$ is a $-(CH_2-CH_2-S)_n-H$ group; and
   wherein m and n are identical or different and each represents an average number of moles of ethylene sulfide added and is an integer from 1 to 10, with the proviso that $2 \leq m+n \leq 20$.

2. The dithiol compound of claim 1, wherein the total number m+n does not exceed 10.

3. The dithiol compound of claim 1, wherein $R^1$ is the residue of a primary fatty amine.

4. The dithiol compound of claim 3, wherein $R^1$ is a copra chain or an oleic chain.

5. The monothiol compound of claim 2, wherein $R^1$ and $R^2$ simultaneously are residues of a secondary fatty amine.

6. A method for making a dithiol compound of claim 1, the method comprising:
   reacting ethylene sulfide with at least one compound of formula (II):

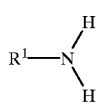

wherein $R^1$ is a straight or branched alkyl or alkenyl group having 10 to 30 carbon atoms; and
   wherein the average number of moles of ethylene sulfide added corresponds to the total m+n.

7. The method of claim 6, wherein the compound of formula (I) obtained by the method is further reacted with ethylene sulfide, whereby the value of m+n is increased by the addition of ethylene sulfide.

8. The method of claim 6, wherein the compound of formula (II) is selected from the group consisting of
   decyl amine, undecyl amine, lauryl amine, myristyl amine, cetyl amine, stearyl amine,
   primary amines derived from a fatty acid obtained from a coconut oil,
   primary amines derived from oleic acid, and
   primary amines derived from a fatty acid obtained from a soybean oil.

9. The method of claim 6, wherein the method is carried out in an inert organic solvent selected from the group consisting of aromatic compounds, ether compounds, alcohol compounds, nitrile compounds, amide compounds, and dimethyl sulfoxide.

10. The method of claim 6, wherein the method is carried out at a temperature in the range of 10 to 200° C.

11. The method of claim 6, wherein the method is carried out at a temperature of 50 to 120° C.

12. A monothiol compound comprising an amino group and having the formula (I):

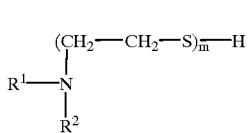

wherein each of $R^1$ and $R^2$, independently, is a hydrogen atom or a straight or branched alkyl or alkenyl group having 10 to 30 carbon atoms, provided that $R^1$ and $R^2$ are not simultaneously hydrogen atoms; and m represents an average number of moles of ethylene sulfide added and is an integer from 2 to 10.

13. A method for making a monothiol compound of claim 12, the method comprising:
   reacting ethylene sulfide with at least one compound of formula (IIa):

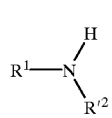

wherein each of $R^1$ and $R^2$ is, independently, a straight or branched alkyl or alkenyl group having 10 to 30 carbon atoms; and
   wherein the average number of moles of ethylene sulfide added corresponds to m.

14. The method of claim 13, wherein the compound of formula (Ia) obtained by the method is further reacted with ethylene sulfide, whereby the value of m is increased by the addition of ethylene sulfide.

15. The method of claim 13, wherein the compound of formula (IIa) is selected from the group consisting of didecyl amine, diundecyl amine, dilauryl amine, dimyristyl amine, dicetyl amine, distearyl amine; secondary amines derived from a fatty acid obtained from a coconut oil; secondary amines derived from oleic acid; and secondary amines derived from a fatty acid obtained from a soybean oil.

16. The method of claim 13, wherein the method is carried out in an inert organic solvent selected from the group consisting of aromatic compounds, ether compounds, alcohol compounds, nitrile compounds, amide compounds, and dimethyl sulfoxide.

17. The method of claim 13, wherein the method is carried out at a temperature in the range of 10 to 200° C.

18. The method of claim 17, wherein the method is carried out at a temperature of 50 to 120° C.

* * * * *